United States Patent [19]
Njamfa

[11] Patent Number: 6,078,388
[45] Date of Patent: Jun. 20, 2000

[54] CALIBRATION SYSTEM FOR SPECTROSCOPIC DETECTORS

[75] Inventor: Serge Njamfa, Cormeilles en Parisis, France

[73] Assignee: I & T Information et Technologie, Le Blanc-Mesnil, France

[21] Appl. No.: 08/912,453

[22] Filed: Aug. 18, 1997

[30]  Foreign Application Priority Data

Aug. 19, 1996 [FR] France .................................. 96-10272

[51] Int. Cl.[7] .............................. G01J 3/00; G01D 18/00
[52] U.S. Cl. ....................................... 356/300; 250/252.1
[58] Field of Search ........................... 356/300; 250/252.1

[56]  References Cited

U.S. PATENT DOCUMENTS 3,645,627  2/1972  Brody et al. .
5,212,537  5/1993  Birang et al. .

FOREIGN PATENT DOCUMENTS 0658751  12/1994  European Pat. Off. .
8600406   6/1985  WIPO .

Primary Examiner—Robert H. Kim
Assistant Examiner—Zandra V. Smith
Attorney, Agent, or Firm—Myers, Dawes & Andras LLP

[57]  ABSTRACT

A standardization device for calibrating a spectroscopic apparatus. The spectroscopic apparatus includes a light source, an optical device to be standardized, and a sensor. The standardization device includes an optical standardization device, an adaptor, and an optical fiber. The optical standardization device transmits at least one monochromatic light beam. The adaptor is removable disposed within the spectroscopic apparatus and interposed between the optical device to be standardized and the optical standardization device. The adaptor transmits the monochromatic light beam between the optical standardization device and the optical device to be standardized. One end of the optical fiber is connected to the standardization device while the other end is connected to the adaptor. The optical fiber transmits the monochromatic light beam between the optical standardization device and the adaptor.

59 Claims, 6 Drawing Sheets

CALIBRATION SYSTEM FOR SPECTROSCOPIC DETECTORS

BACKGROUND OF THE INVENTION

1. Field of the Invention

The present invention generally concerns the standardization of spectroscopic apparatuses and more particularly a device for standardization of a spectroscopic apparatus, which successively includes a light source, an optical device to be standardized capable of providing at least one monochromatic light beam, and a sensor capable of picking up at least one monochromatic light beam.

2. Description of Related Art

Spectroscopic apparatus in this case is understood to mean any apparatus capable, for example, of recording or measuring the intensity of a light spectrum containing one or more spectroscopic lines, such as, for example, a photometric detector, a spectrofluorometric detector, or else a spectrophotometric detector.

Generally, in order to standardize a photometric detector which conventionally includes a deuterium lamp which sends a polychromatic light beam to an optical grating capable of providing a number of independent monochromatic light beams which are detected by an array of photodiodes, one uses a mercury lamp of which one knows ten lines with ten given wavelengths $\lambda$.

This mercury lamp is positioned in place of the deuterium lamp, and in this way it is possible to standardize the optical grating of the photometric detector based on the ten known wavelengths.

The main disadvantage of such a standardization device is that the standardization of the optical grating is done exclusively on the ten lines of the mercury lamp which is used.

Furthermore, one knows from prior art a standardization device which has at least one holmium filter whose absorption lines are known, inserted between the light source and the optical device to be standardized.

A disadvantage of the aforementioned standardization devices of the state of the art is that they all function at wavelengths $\lambda$ belonging to the visible domain.

SUMMARY OF THE INVENTION

Consequently, the present invention proposes a new device for standardization of a spectroscopic apparatus, which is simple and economical and which allows one to standardize said spectroscopic apparatus on any given wavelength $\lambda$ belonging to the visible or else to the ultraviolet domain.

More particularly, according to the invention, the standardization device includes an optical standardization device capable of providing at least one monochromatic light beam, an adaptor interposed between the optical device to be standardized and the optical standardization device, for transmitting a monochromatic light beam between said optical standardization device and that to be standardized and vice versa, and an optical fiber of which one end is connected to the standardization device and the other end is connected to the adaptor for the transmission of the monochromatic light beam between said optical standardization device and said adaptor and vice versa.

Thus, by adjusting the optical standardization device on a desired wavelength $\lambda$, it is possible to standardize the optical device to be standardized with the spectroscopic apparatus based on said wavelength.

According to an advantageous embodiment of said standardization device according to the present invention, the adaptor includes, on one hand, a casing of which at least two perpendicular walls are provided with two respective openings, one opening being connected to the optical fiber and the other opening being positioned facing said optical device to be standardized, and on the other hand, at least one mirror placed inside said casing and oriented facing said openings so that an optical ray entering through one of the openings leaves by the other, and vice versa.

According to another embodiment, the adaptor is a casing provided with a conduit passing through, opening to the outside at both ends, one end being intended to be connected to the optical fiber and the other end being arranged facing said optical device to be standardized.

BRIEF DESCRIPTION OF THE DRAWINGS

The following description with regard to the appended drawings, which are given as nonlimiting examples, will allow one to understand well of what the invention consists and how it can be produced.

In the appended drawings.

BRIEF DESCRIPTION OF THE PREFERRED EMBODIMENTS

Figure 1A:
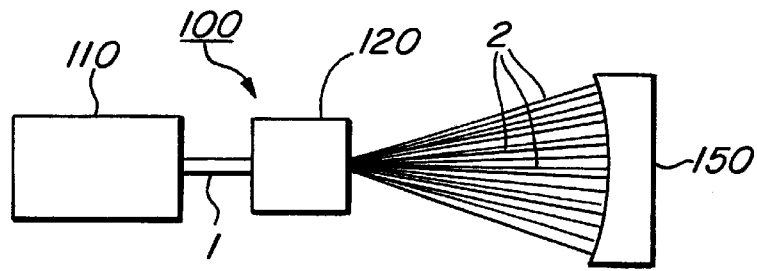
FIG. 1a represents a block diagram of a photometric detector.

FIG. 1a represents the general principle of functioning of photometric detector 100 which has light source 110 capable of emitting incident polychromatic light beam 1 in the direction of optical grating 120 to be standardized, which is capable of providing a number of independent monochromatic light beams 2 which are picked up by photodiode array 150.

Figure 1B:
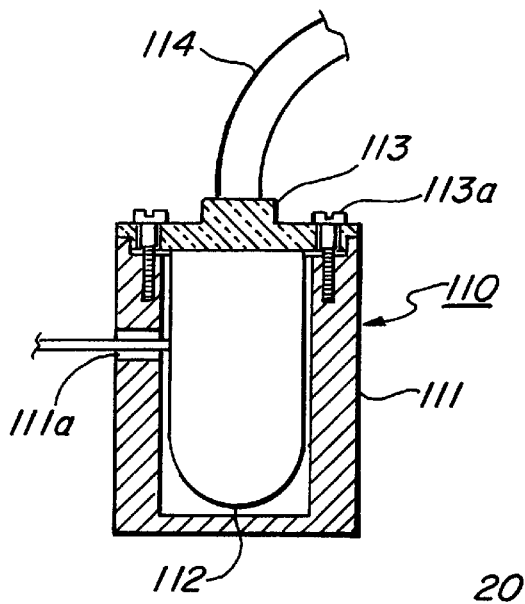
FIG. 1b represents a detailed view in section of the light source of the photometric detector of FIG. 1a, FIG. 2 represents a block diagram of the standardization device according to the invention, placed inside of the photometric detector of FIG. 1a, FIG. 3a represents a detailed view in section of a first embodiment of the adaptor of the standardization device of FIG. 2.

As shown more particularly in FIG. 1b light source 110 is made up of casing 111 inside of which is positioned lamp 112, in this case a deuterium lamp capable of emitting a polychromatic light beam through opening 111a provided in the lateral wall of casing 111, in the direction of optical grating 120. It will be noted that deuterium lamp 112 is supported by support 113 suspended on the upper edges of casing 111 and attached by the intermediary of screw 113a. This deuterium lamp is supplied by power supply cable 114.

The functioning of photometric detector 100 is the following. The incident polychromatic light provided by deuterium lamp 112 passes through optical grating 120 which allows one to obtain coming out of it all the wavelengths of the incident light spectrum emitted (the wavelengths varying between approximately 190 and 800 nm). Each individualized monochromatic light beam provided by optical grating 120 is collected by a light-detecting diode of photodiode array 150.

Figure 2:
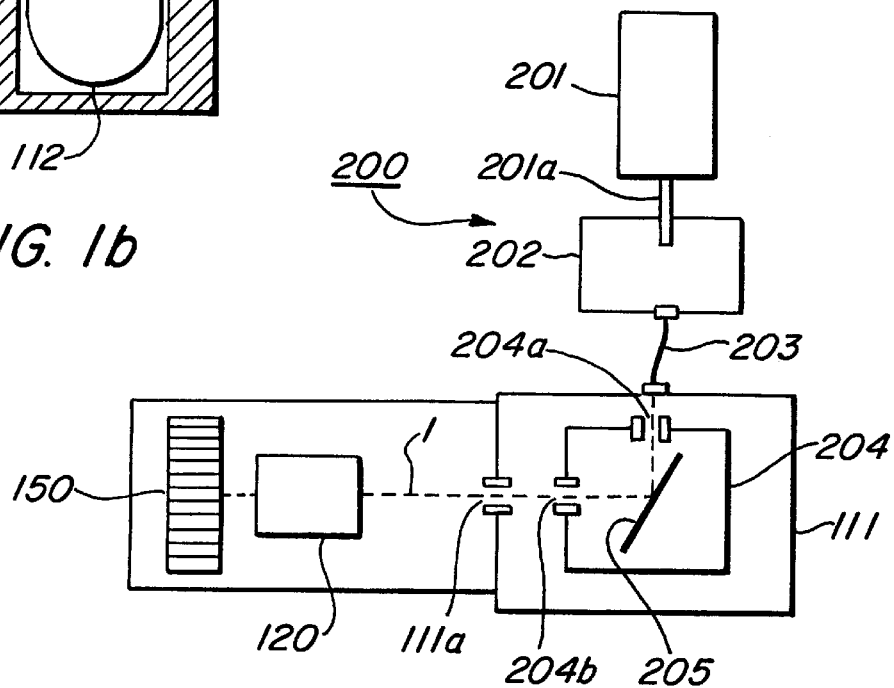

FIG. 2 represents a standardization device according to the present invention which allows one to standardize optical grating 120 of photometric detector 100.

This standardization device has an optical standardization device which in this case is calibrated monochromator 202, capable of providing monochromatic light beam 1' with a given wavelength $\lambda$.

This calibrated monochromator 202 is supplied by light source 201 which provides incident light beam 201a. This light source 201 is, for example, a deuterium lamp. Furthermore, optical fiber 203 is provided, of which one end is connected to the output of optical standardization device 202 and of which the other end is connected to adaptor 204. This optical fiber 203 is capable of transmitting the monochromatic light beam coming from standardization device 202 to adaptor 204.

Adaptor 204 is positioned in place of said light source 110 of photometric detector 100. Entry 204a of adaptor 204 is connected to the output of optical fiber 203, and exit 204b of the adaptor is placed facing the entry of the optical grating to be standardized 120.

Figure 3A:
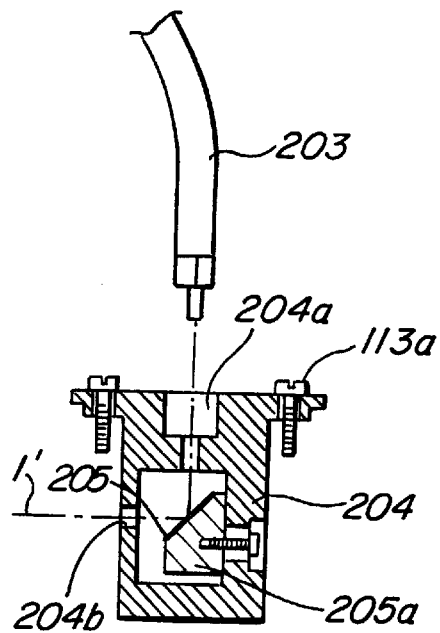
FIG. 3b represents a detailed view in section of the adaptor of FIG. 3a, placed in the photometric detector of FIG. 1a, FIG. 4a represents a detailed view in section of a second embodiment of the adaptor of the standardization device of FIG. 2.
Figure 3B:
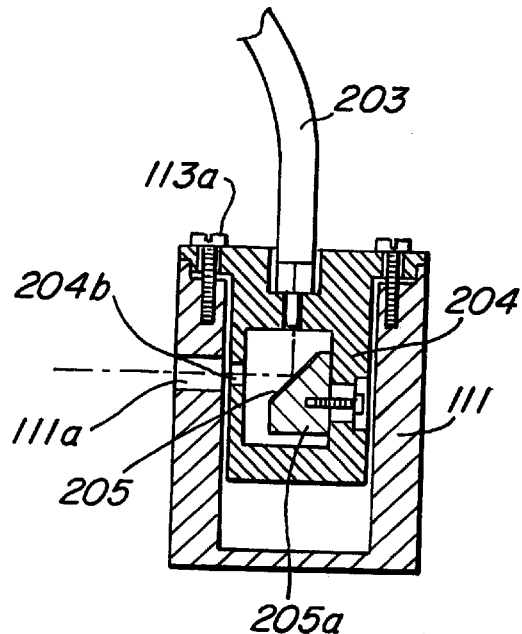

More particularly, as shown by FIGS. 3a and 3b, adaptor 204 has a casing of which two perpendicular walls are provided with two respective openings 204a, 204b. A first opening 204a is an entry opening connected to the output of optical fiber 203. Second opening 204b is an exit opening placed facing optical grating 120 to be standardized. Inside of the casing of adaptor 204, mirror 205 is positioned, whose reflecting surface is placed facing said openings 204a and 204b of adaptor 204. Mirror 205 is supported by support 205a screwed onto a wall of the adaptor casing. Mirror 205 is oriented in such a way that an optical ray entering through entry opening 204a of the adaptor casing leaves through exit opening 204b of the adaptor casing. Mirror 205 is therefore oriented at an angle of 45° with respect to the perpendicular axes passing through said entry and exit openings 204a, 204b. The casing of adaptor 204 is positioned in place of lamp 112 in casing 111 of photometric detector 100 so that the exit opening 204b of the casing of adaptor 204 is facing opening 111a of casing 111 of photometric detector 100.

Figure 4A:
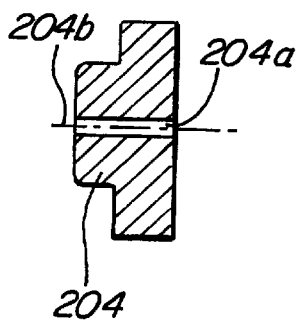
FIG. 4b represents a front view of the adaptor of FIG. 4a, FIG. 5 represents a block diagram of a spectrofluorometric detector.
Figure 4B:
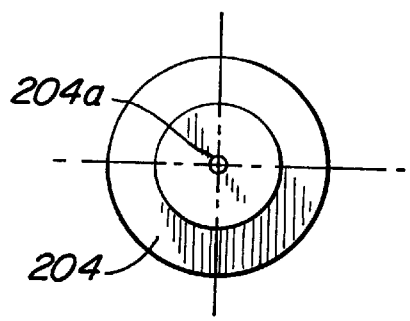

According to a variant of adaptor 204 represented in FIGS. 4a and 4b, it has a casing provided with a conduit passing through, opening to the exterior through its two ends 204a, 204b, a first end 204a being intended to be connected to an optical fiber and second end 204b being arranged facing the optical device to be standardized, in this case optical grating 120. This adaptor variant is used when it is possible to transmit directly the monochromatic light beams emitted by the standardization device to the optical grating to be standardized.

Standardization device 200 functions in the following manner.

On calibrated monochromator 202, one selects a given wavelength $\lambda$. Light source 201 supplies calibrated monochromator 202 which supplies as output monochromatic light beam 1' with the given wavelength $\lambda$. This beam is transmitted to the entry of adaptor 204 via optical fiber 203. It is reflected inside of the adaptor on mirror 205 and leaves through exit opening 204b and arrives, via opening 111a of the casing of the photometric detector, on optical grating 120. Photodiode array 150 records the wavelength $\lambda$ of the monochromatic beam provided as output by optical grating 120. The monochromatic light beam, detected by the photodiode array will be compared with the incident light beam provided by calibrated monochromator 202, and thus by modifying the wavelength adjustment of the calibrated monochromator, it will be possible to test the capacity of the optical grating to provide exact wavelengths on the corresponding diodes of the photodiode array.

Figure 5:
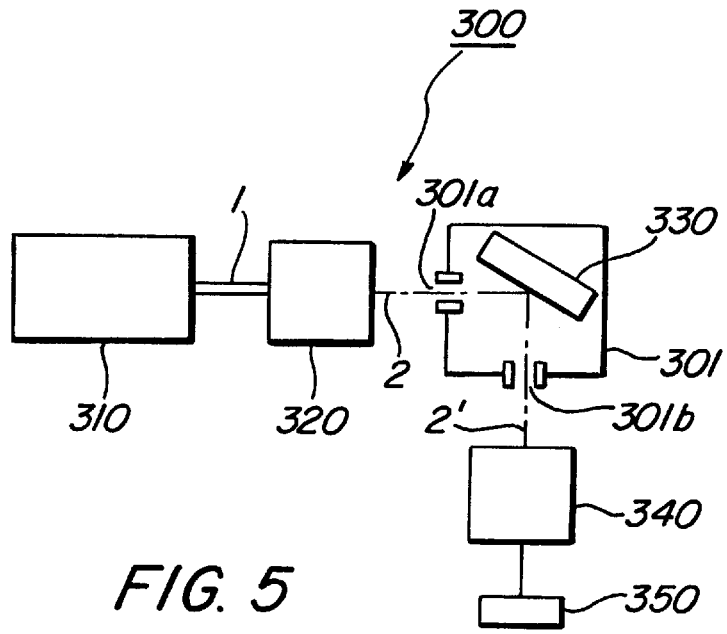

FIG. 5 represents a diagram of spectrofluorometric detector 300. Such a spectrofluorometric detector 300 has light source 310 capable of emitting polychromatic light beam 1 in the direction of excitation monochromator 320 which provides excitation monochromatic light beam 2 in the direction of measurement cell 330. This measurement cell 330 is arranged inside of casing 301 provided with two openings including one entry opening 301a through which arrives excitation monochromatic light beam 2. Under the effect of said excitation monochromatic light beam 2, measurement cell 330 emits by fluorescence a monochromatic light beam 2' in the direction of emission monochromator 340 via exit opening 310b of casing 301 in which said measurement cell 330 is located.

Emission monochromator 340 is capable of transmitting said resulting fluorescence monochromatic light beam to photodiode 350.

In reference to FIGS. 6, 7a, 7c and 7d, standardization device 400 of spectrofluorometric detector 300 represented in FIG. 5 includes light source 401 which supplies, by polychromatic light beam 401a, calibrated monochromator 402 which is capable of providing a monochromatic light beam with a given wavelength $\lambda$. Coming out of calibrated monochromator 402, first optical fiber 403 for transmission is provided, whose output is connected to adaptor 404. Adaptor 404 has first entry 404a where first optical fiber 403 is connected and first exit 404b placed facing emission monochromator 340 to be standardized.

Figure 6:
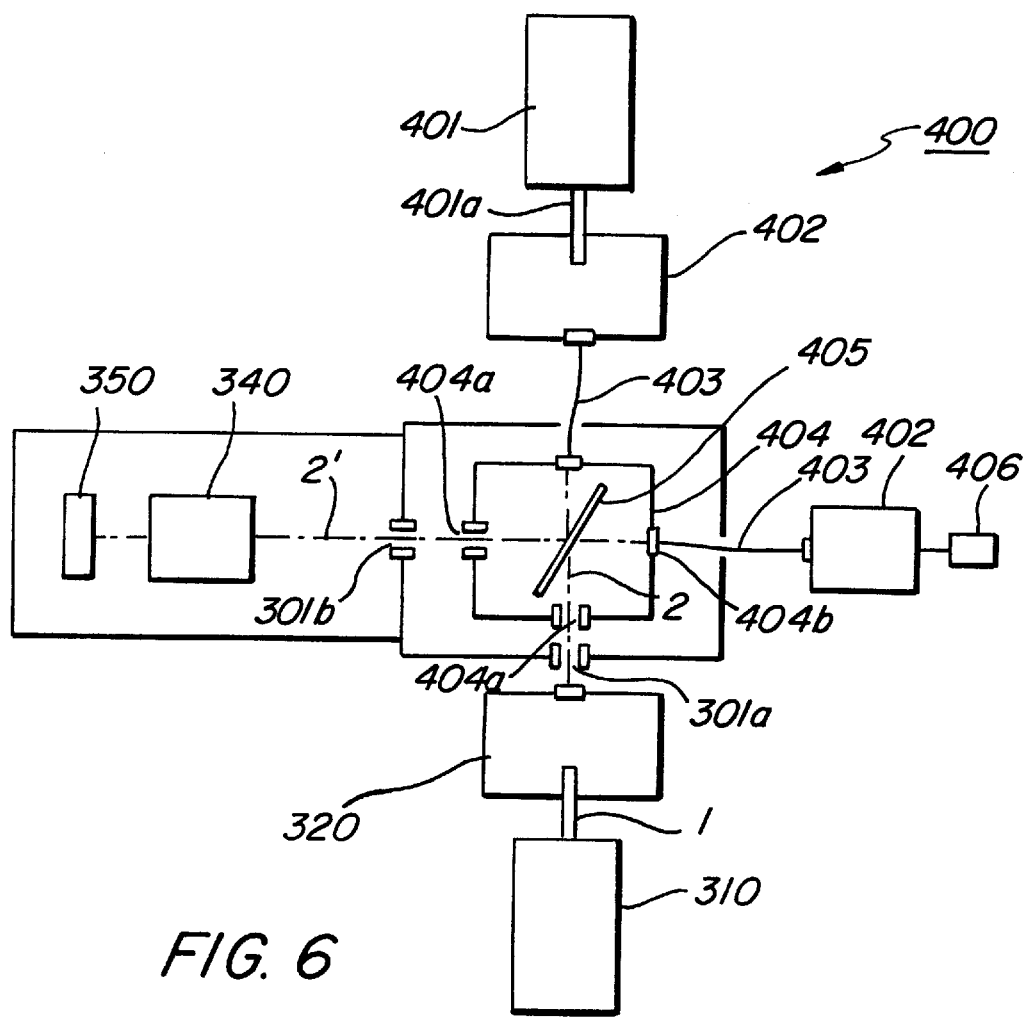
FIG. 6 represents a block diagram of the standardization device according to the invention of the spectrofluorometric detector of FIG. 5.

As shown more particularly by FIG. 6, adaptor 404 is arranged inside of casing 301 in place of measurement cell 330. First entry 404a and first exit 404b of the adaptor are arranged on two perpendicular walls of the casing of adaptor 404. First exit 404b of the adaptor casing is aligned with exit 301b of casing 301 of spectrofluorometric detector 300.

In the same way as for the photometric detector 100 represented in FIGS. 1–4, by adjusting the calibrated monochromator 402 on a given wavelength λ, it is possible to test the capacity of emission monochromator 340 to provide an exact wavelength and thus to standardize it.

Figure 7A:
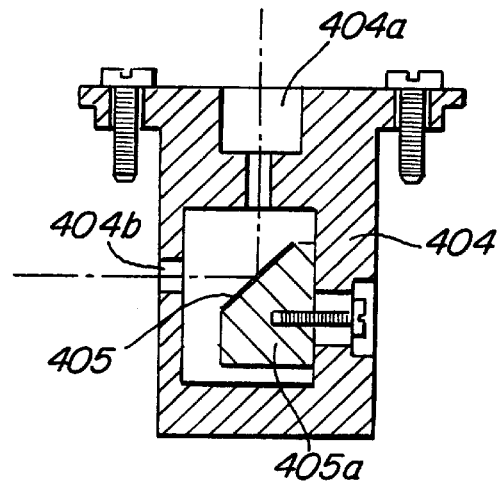
FIG. 7a represents an adaptor of the standardization device of FIG. 6.
Figure 7B:
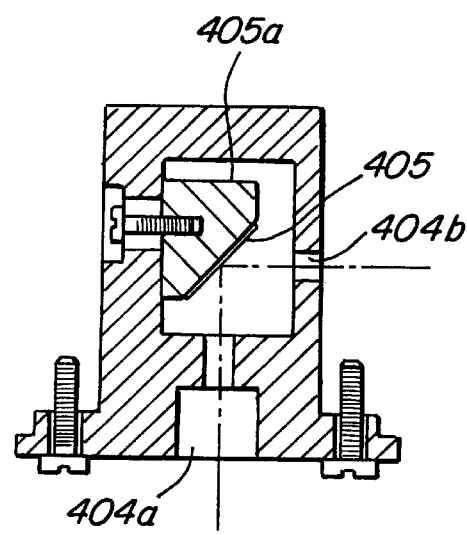
FIG. 7b represents another adaptor of the standardization device of FIG. 6.
Figure 7C:
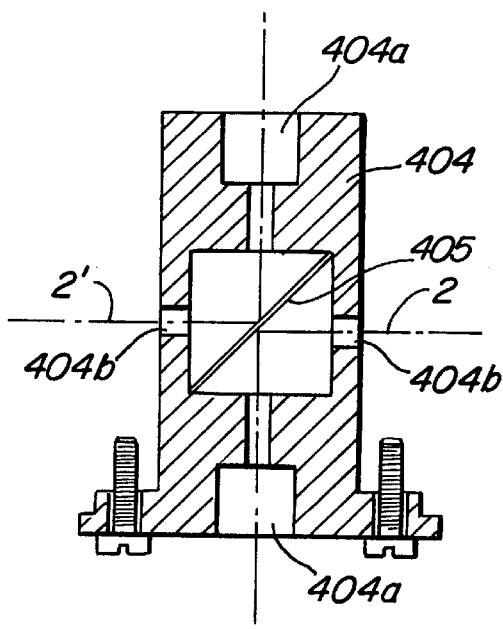
FIG. 7c represents a variant of the adaptor of the standardization device of FIG. 6.
Figure 7D:
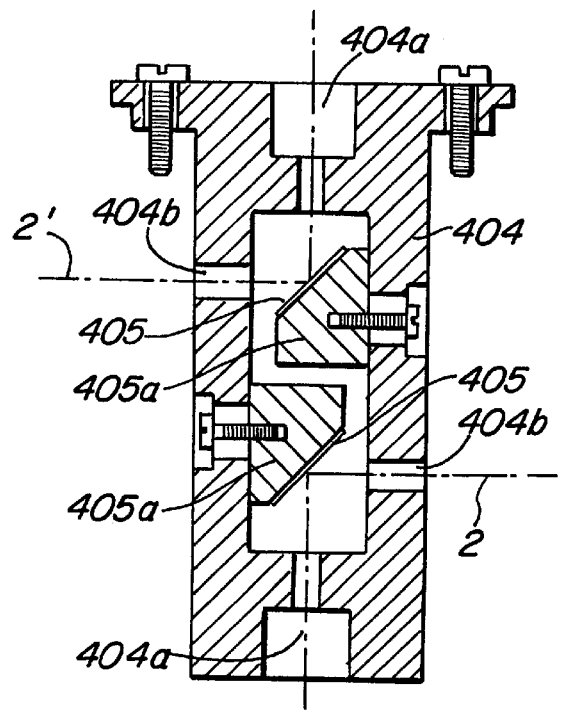
FIG. 7d represents another variant of the adaptor of the standardization device of FIG. 6.

Adaptor 404 of standardization device 400 also, according to the embodiments represented in FIGS. 6, 7c and 7d, has second entry 404a arranged facing excitation monochromator 320 and second exit 404b which is connected to second optical fiber 403 for transmission, which is itself connected to another optical standardization device 402.

According to the embodiment represented more particularly in FIG. 7c, the adaptor has in its adaptor casing, on two upper and lower parallel walls, the first and second entries 404a positioned facing one another, and on the two parallel lateral walls, the first and second exits 404b positioned facing one another.

According to this embodiment, inside the adaptor casing, a mirror 405 is provided, which has two opposite reflecting surfaces. A first reflecting surface of mirror 405 is arranged facing first entry 404a and first exit 404b of the adaptor. A second reflecting surface of mirror 405 is arranged facing second entry 404a and second exit 404b of the adaptor casing. Mirror 405 is oriented so that optical ray 2, 2' entering through entry 404a of adaptor 404 leaves through associated exit 404b of the adaptor.

More particularly, mirror 405 is in this case oriented at a 450 angle with respect to two perpendicular axes, a first axis passing through the first and second entries 404a and a second perpendicular axis passing through the first and second exits 404b of adaptor 404.

According to a variant of the embodiment of adaptor 404 represented in FIG. 7d, it is possible to provide adaptor exits 404b which are positioned in two lateral parallel walls of the casing of adaptor 404, offset in terms of height. Thus, according to this embodiment, inside of the adaptor casing, two mirrors 405 are provided, first mirror 405 having a reflecting surface turned towards first entry and exit 404a, 404b and oriented in such a way that an optical ray entering through upper entry 404a leaves through first associated exit 404b of the adaptor, and second mirror 405, whose reflecting surface is turned towards second entry and exit 404a, 404b and is oriented in such a way that an optical ray entering through lower entry 404a of the adaptor leaves through second associated exit 404b of the adaptor.

Each of mirrors 405 is attached by the intermediary of support 405a to a lateral wall of the adaptor casing.

Each of the adaptor casings represented in FIGS. 7c and 7d is positioned inside of casing 301 of the spectrofluorometric detector in place of the measurement cell with adaptor exit 404b facing exit 301b of the casing and adaptor entry 404a facing the entry of casing 301a.

According to a first embodiment, it is possible to provide another optical standardization device 402, for standardization of excitation monochromator 320, which is a calibrated monochromator capable of providing a monochromatic light beam with a given wavelength λ, and whose output is connected to photodiode 406.

Thus, by varying calibrated monochromator 402 increment by increment, one succeeds in tuning its wavelength to that emitted by excitation monochromator 320, the signal collected by photodiode 406 then becoming maximum when the wavelengths are tuned.

According to a second embodiment, it is possible to provide another optical standardization device 402, serving for standardization of excitation monochromator 320, which consists of optical grating 402 providing a number of independent monochromatic light beams, which is connected to photodiode array 406.

Thus, the diode of the photodiode array 406 receiving the most energy will correspond to the incident wavelength emitted by excitation monochromator 320.

Furthermore, according to an execution variant represented more particularly in FIGS. 7a and 7b, it is possible to provide two independent adaptors 404, each adaptor 404 being associated with a monochromator to be standardized, the excitation monochromator and the emission monochromator.

FIG. 7a represents an adaptor equivalent to that represented in FIG. 3a, intended for the standardization of emission monochromator 340, which has an adaptor casing provided on two perpendicular walls with entry 404a and exit 404b. Entry 404a is on the upper wall, and inside the adaptor casing, a mirror is provided which has a reflecting surface turned towards the entry 404a and exit 404b of adaptor casing 404. This mirror 405 is supported by support 405a which is screwed into the lateral wall of casing 404 opposite to that provided with exit 404b. The mirror is oriented at a 45° angle with respect to the two perpendicular axes passing through entry 404a and exit 404b so that an optical ray entering through entry 404a of the adaptor leaves through exit 404b. This adaptor is intended to be positioned in casing 301 of the spectrofluorometric detector in such a way that exit 404b of the adaptor is facing exit 301b of casing 301 facing emission monochromator 340.

Furthermore, in order to standardize excitation monochromator 301 of the spectrofluorometric detector 300, it is possible to provide, as shown more particularly by FIG. 7b, adaptor 404 which has an adaptor casing whose lower surface is provided with entry 404a and whose lateral perpendicular surface is provided with exit 404b, entry 404a facing entry 301a of casing 301 of spectrofluorometric detector 300 positioned facing excitation monochromator 320.

The inside of the adaptor casing is provided with mirror 405 whose reflecting surface is turned towards the entries and exits 404a, 404b of the adaptor casing. It is oriented in such a way that an optical ray entering through entry 404a of the adaptor casing leaves through exit 404b. Mirror 405 is supported by support 405a which is screwed into a lateral wall of the casing opposite that provided with exit 404b.

The adaptors represented in FIGS. 7c and 7d will be used more particularly to standardize a spectrofluorometric detector which emits in the domain of the visible and ultraviolet.

Figure 8:
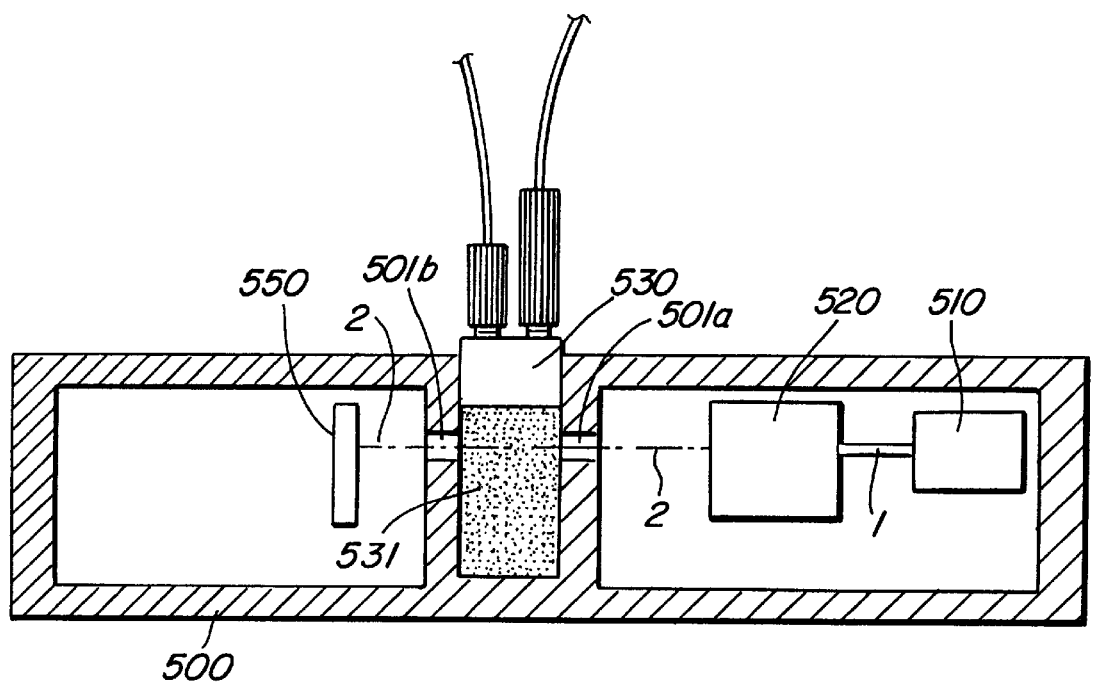
FIG. 8 represents a diagrammatic view in section of a spectrophotometer.

FIG. 8 represents spectrophotometric detector 500, which allows one to measure the absorbance of a mobile or static product contained in a measurement cuvette. As a function of the measured absorbance, it is possible to determine the concentration of the product. This absorbance depends on the wavelength of the monochromatic beam emitted in the direction of the product.

More particularly, as shown by FIG. 8, this spectrophotometric detector 500 has light source 510 which supplies excitation monochromator 520 by excitation polychromatic light beam 1. This excitation monochromator 520 provides as output excitation monochromatic light beam 2 with a given wavelength λ which is propagated via opening 501a provided in the casing of spectrophotometric detector 500 to the interior of measurement cuvette 530 supplied with product 531. Light beam 2 leaving this measurement cuvette passes through opening 501b provided in the casing of the spectrophotometric detector and is picked up by photodiode 550.

Figure 9:
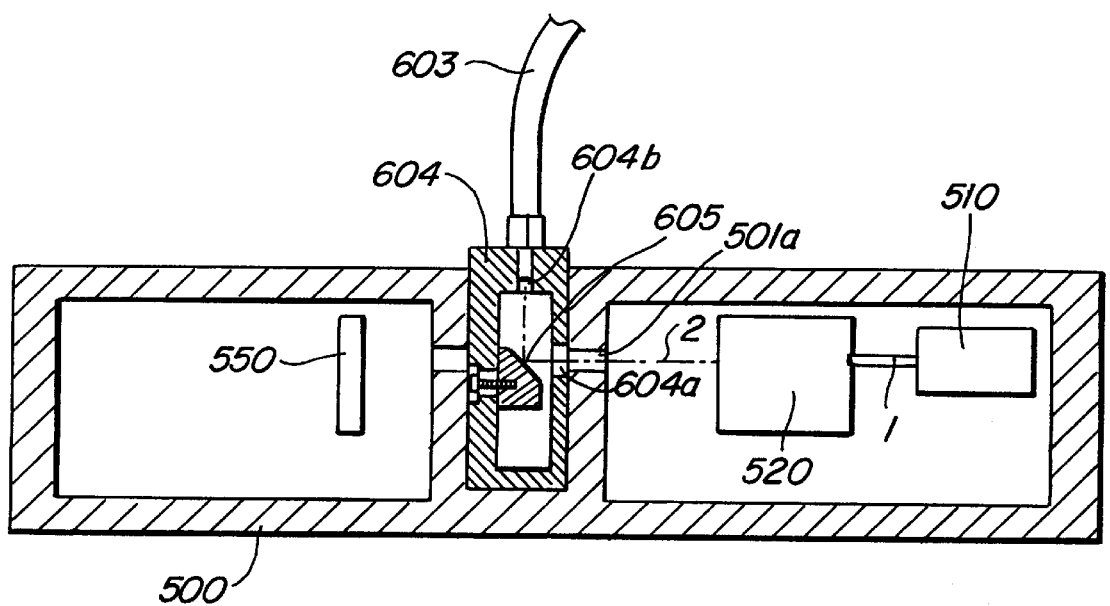
FIG. 9 represents a partial view in section of a standardization device according to the invention incorporated in the spectrophotometer of FIG. 8.
Figure 10:
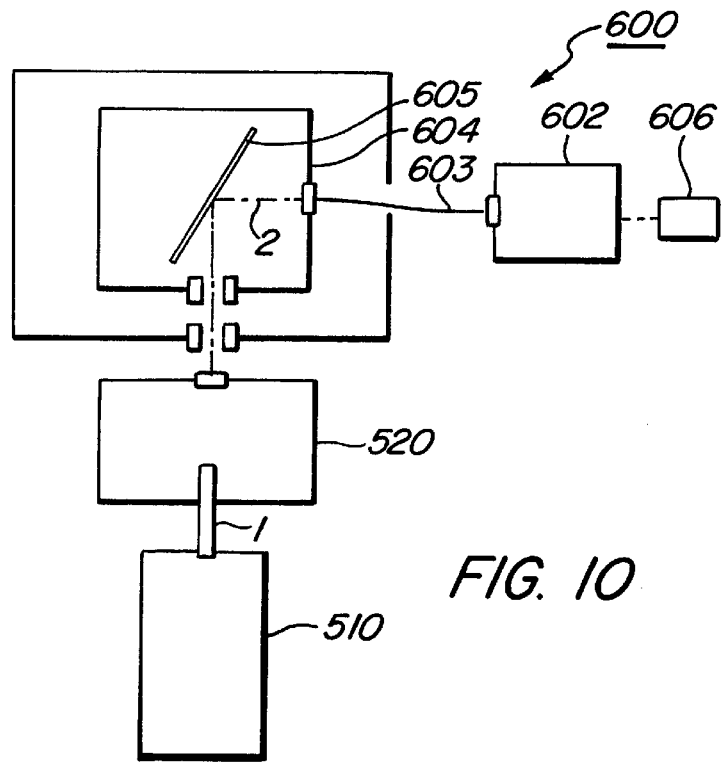
FIG. 10 represents a block diagram of the standardization device according to the invention of the spectrophotometer of FIG. 8.

FIGS. 9 and 10 represent standardization device 600 according to the present invention, which is capable of standardizing spectrophotometric detector 500.

As can be seen in these figures, standardization device 600 has adaptor 604 positioned in place of measurement cuvette 530 in spectrophotometric detector 500. This adaptor 604 has entry opening 604a provided in a lateral wall of the adaptor casing and exit opening 604b provided on the upper wall of casing 604a, upper wall which is perpendicular to the lateral wall. Entry opening 604a of the adaptor casing is positioned facing opening 501a of the casing of the spectrophotometric detector facing the excitation monochromator to be standardized 520, and exit opening 604b of the adaptor casing is connected to optical fiber 603 for transmission, which is itself connected to a standardization device 602.

At the output of this standardization device 602, sensor 606 is provided.

The inside of adaptor casing 604 is provided with mirror 605 whose reflecting surface is placed facing entry opening 604a and exit opening 604b of the adaptor, and which is oriented in such a way that an optical ray entering through entry opening 604a leaves through exit opening 604b and vice versa.

Figures 11A, 11B:
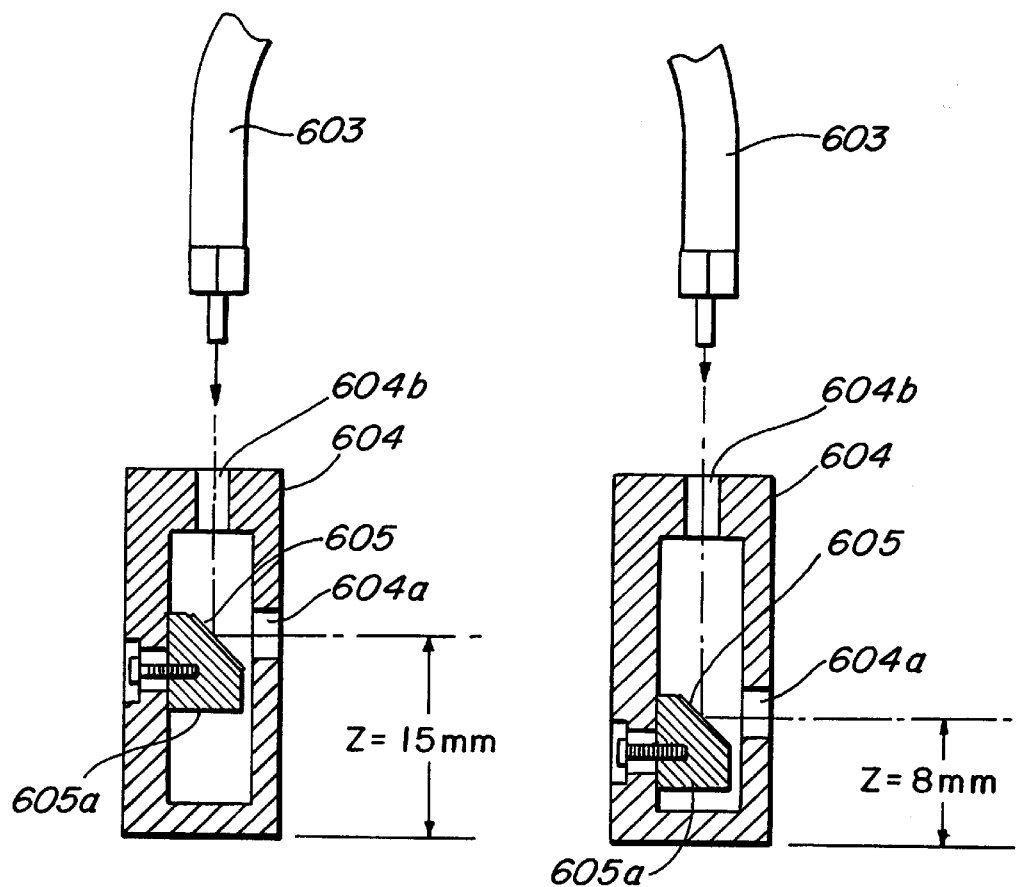
FIG. 11a represents a detailed view in section of a first embodiment of the adaptor of the standardization device of FIG. 10.
FIG. 11b represents a second embodiment of the adaptor of the standardization device of FIG. 10.

According to the embodiment represented in FIG. 11a, the mirror is place inside of the adaptor casing a distance on the order of 15 mm from the bottom of the adaptor casing at the level of entry opening 604a of said adaptor casing.

According to a variant represented in FIG. 11b, the mirror is positioned in the bottom of the adaptor casing at a height on the order of 8 mm from the bottom of the adaptor casing at the level of entry opening 604a of the adaptor casing.

These two variants correspond to two spectrophotometric detector variants exit 501a positioned at the respective heights of 15 and 8 mm.

Coming out of optical fiber 603 connected to exit opening 604b of the adaptor, it is possible to provide calibrated monochromator 602 which is capable of providing a calibrated monochromatic light beam with a given wavelength $\lambda$. This calibrated monochromator 602 is then connected at the output to photodiode 606.

Thus, by varying increment by increment the wavelength $\lambda$ of calibrated monochromator 602, one adjusts it on the wavelength $\lambda$ of the incident signal provided by the excitation monochromator 520 of the spectrophotometric detector, and the photodiode then receives a maximum signal.

It is also possible to provide, as a variant, the standardization device 602 which is an optical grating capable of providing a number of independent monochromatic light beams. The output of the optical grating is connected to a photodiode array 606.

In this case, the diode of the photodiode array 606 receiving the most energy will correspond to the incident wavelength emitted by excitation monochromator 520 to be standardized.

The present invention is in no way limited to the embodiments described and represented, but rather the expert in the field will be able to contribute any variant to them in accordance with the intent of the invention.

I claim:

1. A standardization device for a spectroscopic apparatus to be calibrated, the spectroscopic apparatus including a light source, an optical device to be standardized and a sensor, said standardization device comprising:

an optical standardization device transmitting at least one monochromatic light beam;

an adaptor removably disposed within the spectroscopic apparatus and interposed between the optical device to be standardized and the optical standardization device, the adaptor transmitting the monochromatic light beam between the optical standardization device and the optical device to be standardized; and an optical fiber of which one end is connected to the standardization device and the other end is connected to the adaptor for the transmission of the monochromatic light beam between said optical standardization device and the adaptor and vice versa.

2. A standardization device according to claim 1, characterized in that the adaptor includes, on one hand, a casing of which at least two perpendicular walls are provided with two respective openings, one opening being connected to the optical fiber and the other opening being positioned facing the optical device to be standardized and, on the other hand, at least one mirror placed inside said casing, which is oriented facing said openings so that an optical ray entering through one of the openings leaves by the other, and vice versa.

3. A standardization device according to claim 2, wherein the spectroscopic apparatus to be calibrated includes a photometric detector, wherein the light source of the photometric detector emits incident polychromatic light beam in the direction of an optical grating which provides a number of independent monochromatic light beams which are picked up by a photodiode array, characterized in that, in place of the light source, the adaptor is provided, whose entry is connected to the exit of optical fiber and whose exit is placed facing the entry of the optical grating to be standardized, and in that the optical standardization device is a calibrated monochromator providing a monochromatic light beam with a given wavelength $\lambda$ supplied by a second light source, and whose output is connected to the input of the optical fiber.

4. A standardization device according to claim 3, characterized in that the light source of said photometric detector consisting of a lamp arranged inside of the casing and capable of emitting polychromatic light beam via opening of the casing in the direction of an optical grating to be standardized, the adaptor has an adaptor casing intended to be positioned in place of the lamp in the casing of the photometric detector, and said adaptor casing has two perpendicular walls, each provided with an opening, an entry opening being connected to the output of the optical fiber and an exit opening being placed facing the opening of the casing of the photometric detector, a mirror being positioned inside of said adaptor casing facing said entry and exit openings in such a way that an optical ray entering through the entry opening leaves through the exit opening.

5. A standardization device according to claim 2 to standardize a spectrofluorometric detector, which has a light source which supplies an excitation monochromator to be standardized, the excitation monochromator providing an excitation monochromatic light beam in the direction of a measurement cell which, under the effect of said excitation monochromatic light beam, emits by fluorescence a monochromatic light beam in the direction of an emission monochromator to be standardized, the emission monochromator transmitting said resulting fluorescence monochromatic light beam to a photodiode, characterized in that, in place of said measurement cell, it is provided with an adaptor which has a first entry connected to the optical fiber and a first exit placed facing the emission monochromator to be standardized, and in that the optical standardization device is a calibrated monochromator providing a monochromatic light beam with a given wavelength λ, supplied by the light source and having an output connected to the input of a first optical fiber.

6. A standardization device according to claim 5, characterized in that said adaptor also has a second entry placed facing the excitation monochromator to be standardized and a second exit connected to a second optical fiber connected to another standardization device capable of providing a monochromatic light beam with a given wavelength λ, whose output is connected to a sensor which is capable of picking up said monochromatic light beam emitted by the latter.

7. A standardization device according to claim 6, characterized in that said adaptor has a casing whose two opposite parallel walls are provided with first and second entries positioned facing one another, and of which the other two parallel lateral walls are provided with first and second exits.

8. A standardization device according to claim 7, characterized in that first and second exits are positioned facing one another, and in that the inside of the adaptor casing is provided with a mirror with two reflecting surfaces of which a first reflecting surface is positioned facing the first entry and the first exit, and whose second reflecting surface is positioned facing the second entry and the second exit, said mirror being oriented so that an optical ray entering through the first entry, respectively the second entry, leaves through the first exit, respectively through the second exit.

9. A standardization device according to claim 8, characterized in that the optical standardization device, for the excitation monochromator to be standardized, is a calibrated monochromator capable of providing a monochromatic light beam with a given wavelength λ, connected at the output to a photodiode.

10. A standardization device according to claim 8, characterized in that the optical standardization device, for the excitation monochromator to be standardized, is an optical grating capable of providing a number of independent monochromatic light beams, which is connected at the output to a photodiode array.

11. A standardization device according to claim 7, characterized in that the first and second exits are positioned in an offset manner, and in that the inside of the adaptor casing is provided with a first mirror whose reflecting surface is placed facing the first entry and exit, and second mirror, whose reflecting surface is positioned facing the second entry and exit, the first mirror being oriented in such a way that an optical ray entering through the first entry leaves through the first exit and the second mirror being oriented in such a way that an optical ray entering through the second entry leaves through the second exit.

12. A standardization device according to claim 11, characterized in that the optical standardization device, for the excitation monochromator to be standardized, is a calibrated monochromator capable of providing a monochromatic light beam with a given wavelength λ, connected at the output to a photodiode.

13. A standardization device according to claim 11, characterized in that the optical standardization device, for the excitation monochromator to be standardized, is an optical grating capable of providing a number of independent monochromatic light beams, which is connected at the output to a photodiode array.

14. A standardization device according to claim 7, characterized in that the optical standardization device, for the excitation monochromator to be standardized, is a calibrated monochromator capable of providing a monochromatic light beam with a given wavelength λ, connected at the output to a photodiode.

15. A standardization device according to claim 7, characterized in that the optical standardization device, for the excitation monochromator to be standardized, is an optical grating capable of providing a number of independent monochromatic light beams, which is connected at the output to a photodiode array.

16. A standardization device according to claim 6, characterized in that the optical standardization device, for the excitation monochromator to be standardized, is a calibrated monochromator capable of providing a monochromatic light beam with a given wavelength λ, connected at the output to a photodiode.

17. A standardization device according to claim 6, characterized in that the optical standardization device, for the excitation monochromator to be standardized, is an optical grating capable of providing a number of independent monochromatic light beams, which is connected at the output to a photodiode array.

18. A standardization device according to claim 2 to standardize a spectrofluorometric detector, which has a light source which supplies an excitation monochromator, the excitation monochromator providing an excitation monochromatic light beam in the direction of a measurement cell which, under the effect of said excitation monochromatic light beam, emits by fluorescence a monochromatic light beam in the direction of emission monochromator, the emission monochromator transmitting said resulting fluorescence monochromatic light beam to a photodiode, characterized in that, in place of said measurement cell, said adaptor is provided, which has an entry placed facing the emission monochromator to be standardized and an exit connected to an optical fiber which is connected to the output of the optical standardization device.

19. A standardization device according to claim 18, characterized in that the optical standardization device, for the excitation monochromator to be standardized, is a calibrated monochromator capable of providing a monochromatic light beam with a given wavelength λ, connected at the output to a photodiode.

20. A standardization device according to claim 18, characterized in that the optical standardization device, for the excitation monochromator to be standardized, is an optical grating capable of providing a number of independent monochromatic light beams, which is connected at the output to a photodiode array.

21. A standardization device according to claim 2, which is capable of standardizing a spectrophotometric detector, which has a light source which supplies an excitation monochromator which is capable of providing an excitation monochromatic light beam in the direction of a product positioned inside measurement cuvette, the monochromatic light beam leaving said measurement cuvette being picked up by a photodiode, characterized in that, in place of said measurement cuvette, an adaptor is provided, which has two perpendicular walls provided with respective openings, an entry opening positioning facing the exit of the excitation monochromator to be standardized and an exit opening connected to an optical fiber.

22. A standardization device according to claim 21, characterized in that the inside of the adaptor casing is provided with a mirror whose reflecting surface is positioned facing said openings in such a way that an optical ray entering through the entry opening leaves through the exit opening, said mirror being placed at a height on the order of 15 mm from the bottom of the adaptor casing.

23. A standardization device according to claim 22, characterized in that the optical standardization device provided at the output of an optical fiber is a calibrated monochromator providing a monochromatic light beam with a given wavelength $\lambda$, said calibrated monochrorator being connected at the output to a photodiode.

24. A standardization device according to claim 22, characterized in that the optical standardization device connected at the output of an optical fiber is an optical grating capable of providing a number of independent monochromatic light beams, whose output is connected to a photodiode array.

25. A standardization device according to claim 21, characterized in that the inside of the adaptor casing is provided with a mirror positioned at a height on the order of 8 mm from the bottom of said adaptor, the reflecting surface of the mirror being placed facing said openings, said mirror being oriented in such a way that an optical ray entering through the entry opening leaves through the exit opening.

26. A standardization device according to claim 25, characterized in that the optical standardization device provided at the output of an optical fiber is a calibrated monochromator providing a monochromatic light beam with a given wavelength $\lambda$, said calibrated monochromator being connected at the output to a photodiode.

27. A standardization device according to claim 25, characterized in that the optical standardization device connected at the output of an optical fiber is an optical grating capable of providing a number of independent monochromatic light beams, whose output is connected to a photodiode array.

28. A standardization device according to claim 21, characterized in that the optical standardization device provided at the output of an optical fiber is a calibrated monochromator providing a monochromatic light beam with a given wavelength $\lambda$, said calibrated monochromator being connected at the output to a photodiode.

29. A standardization device according to claim 21, characterized in that the optical standardization device connected at the output of an optical fiber is an optical grating capable of providing a number of independent monochromatic light beams, whose output is connected to a photodiode array.

30. A standardization device according to claim 1, characterized in that the adaptor is a casing provided with a conduit passing through, opening to the outside at both ends, one end being intended to be connected to the optical fiber and the other end being arranged facing said optical device to be standardized.

31. A standardization device according to claim 30, wherein the spectroscopic apparatus to be calibrated includes a photometric detector, wherein the light source of the photometric detector emits incident polychromatic light beam in the direction of an optical grating which provides a number of independent monochromatic light beams which are picked up by a photodiode array, characterized in that, in place of the light source, the adaptor is provided, whose entry is connected to the exit of optical fiber and whose exit is placed facing the entry of the optical grating to be standardized, and in that the optical standardization device is a calibrated monochromator providing a monochromatic light beam with a given wavelength $\lambda$ supplied by a second light source, and whose output is connected to the input of the optical fiber.

32. A standardization device according to claim 31, characterized in that the light source of said photometric detector consisting of a lamp arranged inside of the casing, the lamp emitting polychromatic light beam via opening of the casing in the direction of an optical grating to be standardized, the adaptor has an adaptor casing positioned in place of the lamp in the casing of the photometric detector, and said adaptor casing has two perpendicular walls, each provided with an opening, an entry opening being connected to the output of the optical fiber and an exit opening being placed facing the opening of the casing of the photometric detector, a mirror being positioned inside of said adaptor casing facing said entry and exit openings in such a way that an optical ray entering through the entry opening leaves through the exit opening.

33. A standardization device according to claim 1 wherein the spectroscopic apparatus to be calibrated includes a photometric detector, wherein the light source of the photometric detector emits incident polychromatic light beam in the direction of an optical grating which provides a number of independent monochromatic light beams which are picked up by a photodiode array, characterized in that, in place of the light source, the adaptor is provided, whose entry is connected to the exit of optical fiber and whose exit is placed facing the entry of the optical grating to be standardized, and in that the optical standardization device is a calibrated monochromator providing a monochromatic light beam with a given wavelength $\lambda$ supplied by a second light source, and whose output is connected to the input of the optical fiber.

34. A standardization device according to claim 33, characterized in that the light source of said photometric detector consisting of a lamp arranged inside of the casing and emitting polychromatic light beam via opening of the casing in the direction of an optical grating to be standardized, the adaptor has an adaptor casing positioned in place of the lamp in the casing of the photometric detector, and said adaptor casing has two perpendicular walls, each provided with an opening, an entry opening being connected to the output of the optical fiber and an exit opening being placed facing the opening of the casing of the photometric detector, a mirror being positioned inside of said adaptor casing facing said entry and exit openings in such a way that an optical ray entering through the entry opening leaves through the exit opening.

35. A standardization device according to claim 1 to standardize a spectrofluorometric detector, which has a light source which supplies an excitation monochromator to be standardized, the excitation monochromator providing an excitation monochromatic light beam in the direction of a measurement cell which, under the effect of said excitation monochromatic light beam, emits by fluorescence a monochromatic light beam in the direction of an emission monochromator to be standardized, the emission monochromator transmitting said resulting fluorescence monochromatic light beam to a photodiode, characterized in that, in place of said measurement cell, it is provided with an adaptor which has a first entry connected to the optical fiber and a first exit placed facing the emission monochromator to be standardized, and in that the optical standardization device is a calibrated monochromator providing a monochromatic light beam with a given wavelength $\lambda$, supplied by the light source and having an output connected to the input of a first optical fiber.

36. A standardization device according to claim 35, characterized in that said adaptor also has a second entry placed facing the excitation monochromator to be standardized and a second exit connected to a second optical fiber connected to another standardization device capable of providing a monochromatic light beam with a given wavelength $\lambda$, whose output is connected to a sensor which is capable of picking up said monochromatic light beam emitted by the latter.

37. A standardization device according to claim 36, characterized in that said adaptor has a casing whose two opposite parallel walls are provided with first and second entries positioned facing one another, and of which the other two parallel lateral walls are provided with first and second exits.

38. A standardization device according to claim 37, characterized in that first and second exits are positioned facing one another, and in that the inside of the adaptor casing is provided with a mirror with two reflecting surfaces of which a first reflecting surface is positioned facing the first entry and the first exit, and whose second reflecting surface is positioned facing the second entry and the second exit, said mirror being oriented so that an optical ray entering through the first entry, respectively the second entry, leaves through the first exit, respectively through the second exit.

39. A standardization device according to claim 38, characterized in that the optical standardization device, for the excitation monochromator to be standardized, is a calibrated monochromator capable of providing a monochromatic light beam with a given wavelength $\lambda$, connected at the output to a photodiode.

40. A standardization device according to claim 38, characterized in that the optical standardization device, for the excitation monochromator to be standardized, is an optical grating capable of providing a number of independent monochromatic light beams, which is connected at the output to a photodiode array.

41. A standardization device according to claim 37, characterized in that the first and second exits are positioned in an offset manner, and in that the inside of the adaptor casing is provided with a first mirror whose reflecting surface is placed facing the first entry and exit, and second mirror, whose reflecting surface is positioned facing the second entry and exit, the first mirror being oriented in such a way that an optical ray entering through the first entry leaves through the first exit and the second mirror being oriented in such a way that an optical ray entering through the second entry leaves through the second exit.

42. A standardization device according to claim 41, characterized in that the optical standardization device, for the excitation monochromator to be standardized, is a calibrated monochromator capable of providing a monochromatic light beam with a given wavelength $\lambda$, connected at the output to a photodiode.

43. A standardization device according to claim 41, characterized in that the optical standardization device, for the excitation monochromator to be standardized, is an optical grating capable of providing a number of independent monochromatic light beams, which is connected at the output to a photodiode array.

44. A standardization device according to claim 37, characterized in that the optical standardization device, for the excitation monochromator to be standardized, is a calibrated monochromator capable of providing a monochromatic light beam with a given wavelength $\lambda$, connected at the output to a photodiode.

45. A standardization device according to claim 37, characterized in that the optical standardization device, for the excitation monochromator to be standardized, is an optical grating capable of providing a number of independent monochromatic light beams, which is connected at the output to a photodiode array.

46. A standardization device according to claim 36, characterized in that the optical standardization device, for the excitation monochromator to be standardized, is a calibrated monochromator capable of providing a monochromatic light beam with a given wavelength $\lambda$, connected at the output to a photodiode.

47. A standardization device according to claim 36, characterized in that the optical standardization device, for the excitation monochromator to be standardized, is an optical grating capable of providing a number of independent monochromatic light beams, which is connected at the output to a photodiode array.

48. A standardization device according to claim 1 to standardize a spectrofluorometric detector, which has a light source which supplies an excitation monochromator which provides an excitation monochromatic light beam in the direction of a measurement cell which, under the effect of said excitation monochromatic light beam, emits by fluorescence a monochromatic light beam in the direction of emission monochromator which transmits said resulting fluorescence monochromatic light beam to a photodiode, characterized in that, in place of said measurement cell, said adaptor is provided, which has an entry placed facing the emission monochromator to be standardized and an exit connected to an optical fiber which is connected to the output of the optical standardization device.

49. A standardization device according to claim 48, characterized in that the optical standardization device, for the excitation monochromator to be standardized, is a calibrated monochromator capable of providing a monochromatic light beam with a given wavelength $\lambda$, connected at the output to a photodiode.

50. A standardization device according to claim 48, characterized in that the optical standardization device, for the excitation monochromator to be standardized, is an optical grating capable of providing a number of independent monochromatic light beams, which is connected at the output to a photodiode array.

51. A standardization device according to claim 1, which is capable of standardizing a spectrophotometric detector, which has la light source which supplies an excitation monochromator which is capable of providing an excitation monochromatic light beam in the direction of a product positioned inside measurement cuvette, the monochromatic light beam leaving said measurement cuvette being picked up by a photodiode, characterized in that, in place of said measurement cuvette, an adaptor is provided, which has two perpendicular walls provided with respective openings, an entry opening positioning facing the exit of the excitation monochromator to be standardized and an exit opening connected to an optical fiber.

52. A standardization device according to claim 51, characterized in that the inside of the adaptor casing is provided with a mirror whose reflecting surface is positioned facing said openings in such a way that an optical ray entering through the entry opening leaves through the exit opening, said mirror being placed at a height on the order of 15 mm from the bottom of the adaptor casing.

53. A standardization device according to claim 52, characterized in that the optical standardization device provided at the output of an optical fiber is a calibrated monochromator providing a monochromatic light beam with a given wavelength $\lambda$, said calibrated monochromator being connected at the output to a photodiode.

54. A standardization device according to claim 52, characterized in that the optical standardization device connected at the output of an optical fiber is an optical grating capable of providing a number of independent monochromatic light beams, whose output is connected to a photodiode array.

55. A standardization device, according to claim 51, characterized in that the inside of the adaptor casing is provided with a mirror positioned at a height on the order of 8 mm from the bottom of said adaptor, the reflecting surface of the mirror being placed facing said openings, said mirror being oriented in such a way that an optical ray entering through the entry opening leaves through the exit opening.

56. A standardization device according to claim 55, characterized in that the optical standardization device provided at the output of an optical fiber is a calibrated monochromator providing a monochromatic light beam with a given wavelength $\lambda$, said calibrated monochromator being connected at the output to a photodiode.

57. A standardization device according to claim 55, characterized in that the optical standardization device connected at the output of an optical fiber is an optical grating capable of providing a number of independent monochromatic light beams, whose output is connected to a photodiode array.

58. A standardization device according to claim 51, characterized in that the optical standardization device provided at the output of an optical fiber is a calibrated monochromator providing a monochromatic light beam with a given wavelength $\lambda$, said calibrated monochromator being connected at the output to a photodiode.

59. A standardization device according to claim 51, characterized in that the optical standardization device connected at the output of an optical fiber is an optical grating capable of providing a number of independent monochromatic light beams, whose output is connected to a photodiode array.

* * * * *